US008642690B2

(12) United States Patent
Saiki et al.

(10) Patent No.: US 8,642,690 B2
(45) Date of Patent: Feb. 4, 2014

(54) BIS [TRI (HYDROXYPOLYALKYLENEOXY) SILYLALKYL] POLYSULFIDE, METHOD OF MANUFACTURING BIS [TRI (HYDROXYPOLYALKYLENEOXY) SILYLALKYL] POLYSULFIDE, TIRE RUBBER ADDITIVE, AND TIRE RUBBER COMPOSITION

(75) Inventors: Takeaki Saiki, Hiratsuka (JP); Makoto Iwai, Ichihari (JP); Haruhiko Furukawa, Chiba (JP); Anil Kumar Tomar, Midland, MI (US)

(73) Assignees: Dow Corning Corporation, Midland, MI (US); Dow Corning Toray Company, Ltd., Chiyoda-ku, Tokyo (JP)

( * ) Notice: Subject to any disclaimer, the term of this patent is extended or adjusted under 35 U.S.C. 154(b) by 762 days.

(21) Appl. No.: 12/521,610

(22) PCT Filed: Dec. 28, 2007

(86) PCT No.: PCT/JP2007/075436
§ 371 (c)(1),
(2), (4) Date: Nov. 4, 2010

(87) PCT Pub. No.: WO2008/082011
PCT Pub. Date: Jul. 10, 2008

(65) Prior Publication Data
US 2011/0040000 A1 Feb. 17, 2011

(30) Foreign Application Priority Data
Jan. 5, 2007 (JP) .................................. 2007-000766

(51) Int. Cl.
B60C 1/00 (2006.01)
C08K 5/24 (2006.01)

(52) U.S. Cl.
USPC ........................................ 524/262; 524/261

(58) Field of Classification Search
USPC ............................................... 524/262, 261
See application file for complete search history.

(56) References Cited

U.S. PATENT DOCUMENTS

| | | | |
|---|---|---|---|
| 3,842,111 A | 10/1974 | Meyer-Simon et al. | |
| 3,997,581 A | 12/1976 | Pletka et al. | |
| 5,393,816 A * | 2/1995 | Kondo et al. | 524/267 |
| 6,620,875 B2 * | 9/2003 | Hong et al. | 524/492 |
| 2002/0115767 A1 * | 8/2002 | Cruse et al. | 524/262 |
| 2003/0119960 A1 * | 6/2003 | Hong et al. | 524/377 |
| 2004/0198881 A1 * | 10/2004 | Cruse et al. | 524/261 |
| 2005/0085583 A1 * | 4/2005 | Hong | 524/492 |
| 2006/0036034 A1 | 2/2006 | Chaves et al. | |
| 2006/0086450 A1 * | 4/2006 | Hogan et al. | 156/110.1 |
| 2009/0312476 A1 * | 12/2009 | Korth et al. | 524/426 |

FOREIGN PATENT DOCUMENTS

| | | |
|---|---|---|
| JP | 48029726 A | 4/1973 |
| JP | 50108225 A | 8/1975 |
| JP | 08259734 A | 10/1996 |
| JP | 09227722 A | 9/1997 |
| JP | 2001031798 A | 2/2001 |
| JP | 2002145890 A | 5/2002 |
| JP | 2004196937 A | 7/2004 |
| WO | WO 2004094437 A1 | 11/2004 |
| WO | WO 2006019963 A1 | 2/2006 |
| WO | WO 2007098120 A2 | 8/2007 |
| WO | WO 2007098121 A2 | 8/2007 |

OTHER PUBLICATIONS

English equivalent for JP 48-029726 extracted from espacenet.com database, dated Nov. 23, 2009, 10 pages.
English equivalent for JP 50-108225 extracted from espacenet.com database, Nov. 23, 2009, 9 pages.
English language translation and abstract for JP 08-259734 extracted from espacenet.com database, Nov. 23, 2009, 53 pages.
English language translation and abstract for JP 09-227722 extracted from espacenet.com database, Nov. 23, 2009, 42 pages.
English language translation and abstract for JP 2001-031798 extracted from espacenet.com database, Nov. 23, 2009, 47 pages.
English language translation and abstract for JP 2002-145890 extracted from espacenet.com database, Nov. 23, 2009, 28 pages.
English language translation and abstract for JP 2004-196937 extracted from espacenet.com database, Nov. 23, 2009 48 pages.
PCT International Search Report for PCT/JP2007/075436, dated Apr. 17, 2008, 4 pages.

* cited by examiner

Primary Examiner — Angela C Scott
(74) Attorney, Agent, or Firm — Howard & Howard Attorneys PLLC

(57) ABSTRACT

A bis[tri(hydroxypolyalkyleneoxy)silylalkyl] polysulfide, i.e., a polysulfide that contains bonded hydroxypolyalkyleneoxy groups instead of alkoxy groups in the bis(trialkoxysilylalkyl) polysulfide; a method of manufacturing of the aforementioned polysulfide by heating a bis(trialkoxysilylalkyl) polysulfide and a polyalkyleneglycol; a tire rubber additive to a tire rubber composition that comprises a bis[tri(hydroxypolyalkyleneoxy)silylalkyl] polysulfide alone or a mixture of bis[tri(hydroxypolyalkyleneoxy)silylalkyl] polysulfide and a polyalkyleneglycol; and a tire rubber composition that contains the aforementioned additive.

4 Claims, 3 Drawing Sheets

BIS [TRI (HYDROXYPOLYALKYLENEOXY) SILYLALKYL] POLYSULFIDE, METHOD OF MANUFACTURING BIS [TRI (HYDROXYPOLYALKYLENEOXY) SILYLALKYL] POLYSULFIDE, TIRE RUBBER ADDITIVE, AND TIRE RUBBER COMPOSITION

RELATED APPLICATIONS

This application claims priority to and all the advantages of International Patent Application No. PCT/JP2007/075436, filed on Dec. 28, 2007, which claims priority to Japanese Patent Application No. JP2007-000766, filed on Jan. 5, 2007.

TECHNICAL FIELD

The present invention relates to a bis[tri(hydroxypolyalkyleneoxy)silylalkyl] polysulfide, a method of manufacturing the bis[tri(hydroxypolyalkyleneoxy)silylalkyl] polysulfide, a rubber additive comprising the aforementioned bis[tri(hydroxypolyalkyleneoxy)silylalkyl] polysulfide, and a tire rubber composition that contains the aforementioned bis[tri(hydroxypolyalkyleneoxy)silylalkyl] polysulfide.

In particular, the present invention relates to a polysulfide wherein hydroxypolyalkyleneoxy groups are used instead of alkoxy groups in a bis(trialkoxysilylalkyl) polysulfide; to a method of manufacturing the aforementioned polysulfide by causing a reaction between a bis(trialkoxysilylalkyl) polysulfide and a polyalkyleneglycol and thus substituting alkoxy groups with hydroxypolyalkyleneoxy groups; to a tire rubber additive comprising a bis[tri(hydroxypolyalkyleneoxy)silylalkyl] polysulfide alone or a mixture of bis[tri(hydroxypolyalkyleneoxy)silylalkyl] polysulfide and a polyalkyleneglycol; as well as to a rubber composition that can be vulcanized to form a tire, and, in particular, a tire tread. The present invention also relates to a rubber composition for tires, in particular, to a tire-tread rubber composition that provides environmentally improved conditions for the production of tires, and which, when vulcanized, produces tires with excellent balance between wet-skid resistance and low fuel consumption properties.

BACKGROUND ART

A bis(trimethoxysilylpropyl) disulfide, bis(triethoxysilylpropyl) disulfide, bis(trimethoxysilylpropyl) tetrasulfide, bis(triethoxysilylpropyl) tetrasulfide, or similar bis(trialkoxysilylalkyl) polysulfide and a method of manufacturing of the aforementioned polysulfides are well known in the art (see Patent References 1 and 2: Japanese Patent Application Publication [hereinafter referred to as Kokai] S48-29726, i.e., JP48-29726A and Kokai S50-108225, i.e., JP50-108225A respectively). A bis(trialkoxysilylalkyl) polysulfide is also well known as a component of rubber compositions that contains a carbon black and a silica filler (see Patent Reference 3: Kokai H08-259734, i.e., JP08-259734A; Patent Reference 4: Kokai H09-227722, i.e., JP09-227722A; and Patent Reference 5: Kokai 2001-31798, i.e., JP2001-31798A).

Also known in the art are sulfur-cured rubber compositions for manufacture of industrial rubber products and rubber tires that have to possess high strength and wear resistance; such compositions contain a silane-coupling agent, carbon black, precipitated silica, fumed silica, or similar fillers with reinforcement properties (see Patent Reference 5 [see above] and Patent Reference 6: Kokai: 2004-196937, i.e., JP2004-196937A).

At the present time a demand in the field of rubber compositions used for the manufacture of air-filled automobile tires, and especially of tire tread, is for development of new technique that could improve engagement of the tire grooves with a wet road (wet-skid resistant properties) and fuel-consumption characteristics of the tires. It has been found that when a tire is manufactured from a rubber composition such as a silica-filled rubber composition with silicone.vinyl type polymer composite rubbery particles, then the vulcanized rubber obtained from this composition has an increased value of tan $\delta$ at 0° C., and a reduced value of tan $\delta$ at 60° C. Based on this observation, a tire rubber composition and, in particular, a tire-tread rubber composition that has a balance between the wet-skid resistant properties and fuel-consumption characteristics was proposed (see Patent Reference 6).

On the other hand, Patent Reference 7 (US2006/036034A1; WO2006/019963A1) discloses a bis(cyclic alkoxysilylalkyl) polysulfide prepared by causing a reaction between a bis(trialkoxysilylalkyl) polysulfide and an alkanediol. The above reference also discloses a rubber composition for tires based on the use of the aforementioned bis(cyclic alkoxysilylalkyl)polysulfide.

However, when in the processes of the aforementioned Patent References 3, 4, 5, and 6, a bis(trimethoxysilylpropyl) disulfide, bis(triethoxysilylpropyl) disulfide, bis(trimethoxysilylpropyl) tetrasulfide, bis(triethoxysilylpropyl) tetrasulfide, or a similar bis(trialkoxysilylalkyl) polysulfide is mixed with a silica filler and an organic rubber, such mixing causes hydrolysis of the alkoxysilyl groups which is accompanied by generation of low-boiling-point alcohols such as methyl alcohol and ethyl alcohol. Therefore, the technique proposed in the above patent applications causes environmental problems in connection with the preparation of the rubber composition and manufacturing of the vulcanized rubber.

In the invention of Patent Reference 7, mixing of a bis (cyclic alkoxysilylalkyl) polysulfide with a silica filler and an uncured organic rubber generates, due to hydrolysis of the cyclic alkoxysilyl groups, an alkanediol that does not have a sufficiently high boiling points. Therefore, environmental problems associated with the production of the rubber compound and the vulcanized rubber remain unsolved.

SUMMARY OF THE INVENTION

Based on detailed study aimed at solving the above-described problems, the inventors herein have found that when hydroxypolyalkyleneoxy groups are used instead of alkoxy groups in a bis(trialkoxysilylalkyl) polysulfide or cyclic alkoxysilyl groups in a bis(cyclic alkoxysilylalkyl) polysulfide, then even when preparation of the rubber composition is accompanied by hydrolysis of the hydroxypolyalkyleneoxy groups, only components such as polyalkyleneglycol that have an extremely high boiling point and that are not subject to evaporation are formed. Thus the inventors arrived at the present invention.

The present invention provides the following:

1) a bis[tri(hydroxypolyalkyleneoxy)silylalkyl] polysulfide, i.e., a polysulfide wherein hydroxypolyalkyleneoxy groups are used instead of alkoxy groups in a bis(trialkoxysilylalkyl) polysulfide or cyclic alkoxysilyl groups in a bis(cyclic alkoxysilylalkyl) polysulfide;
2) a method of manufacturing the aforementioned polysulfide;
3) a tire rubber additive that makes it possible to solve the environmental problems associated with hydrolysis of alkoxysilyl groups or cyclic alkoxysilyl groups during mixing of an uncured organic rubber, a silica filler, a bis

[trialkoxysilylalkyl] polysulfide or bis(cyclic alkoxysilylalkyl) polysulfide, etc., that, when vulcanized, ensures an increased value of tan δ at 0° C. and a reduced value of tan δ at 60° C., that is characterized by excellent balance between wet-skid resistance and low fuel consumption properties, and that possesses high resistance to wear; and 4) a rubber composition for tires and tire treads that makes it possible to solve the environmental problems associated with hydrolysis of alkoxysilyl groups or cyclic alkoxysilyl groups during mixing of an uncured organic rubber, a silica filler, a bis[trialkoxysilylalkyl] polysulfide or bis(cyclic alkoxysilylalkyl) polysulfide, etc., that, when vulcanized, ensures increased value of tan δ at 0° C. and a reduced value of tan δ at 60° C., that is characterized by excellent balance between wet-skid resistance and low fuel consumption properties, and that possesses high resistance to wear.

DISCLOSURE OF THE INVENTION

Figure 1:
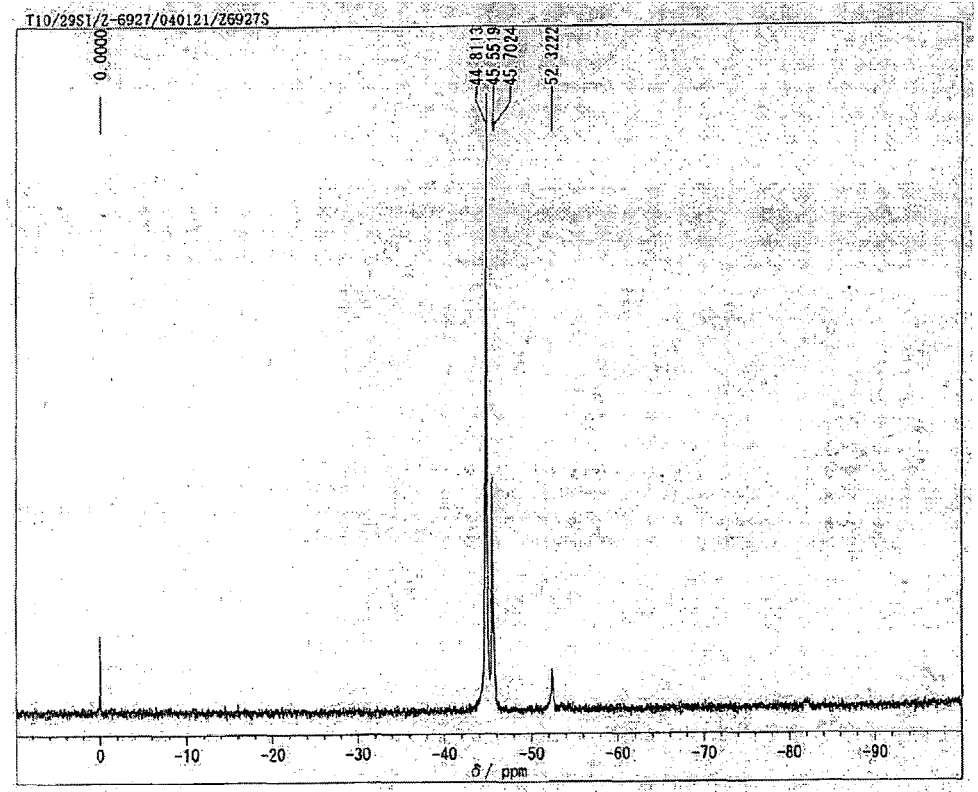
FIG. 1 illustrates a $^{29}$Si-NMR chart for a diethyleneglycol solution prepared in EXAMPLE 1.
Figure 2:
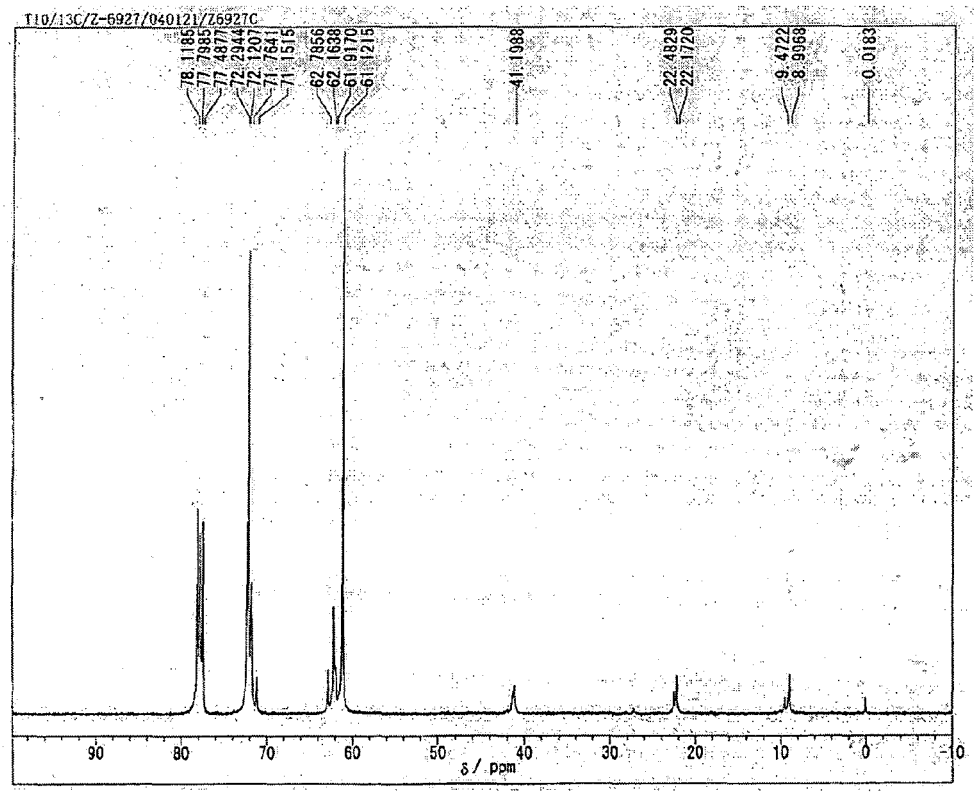
FIG. 2 illustrates a $^{13}$C-NMR chart for the diethyleneglycol solution prepared in EXAMPLE 1.
Figure 3:
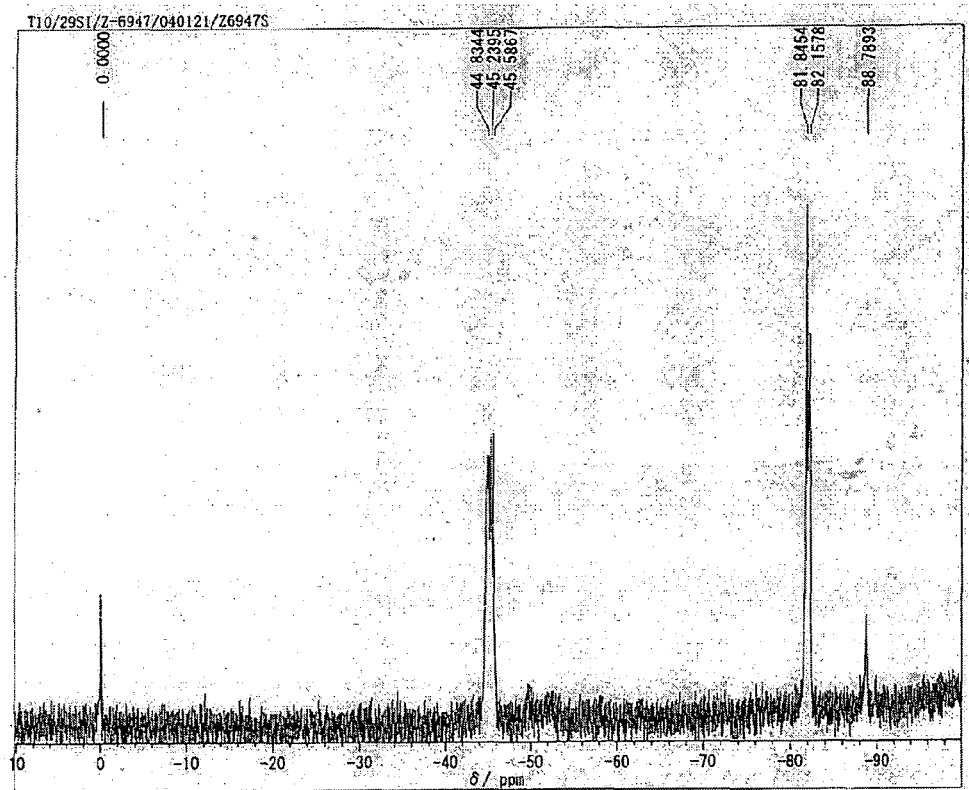
FIG. 3 illustrates a $^{29}$Si-NMR chart for the diethyleneglycol solution prepared in EXAMPLE 2.
Figure 4:
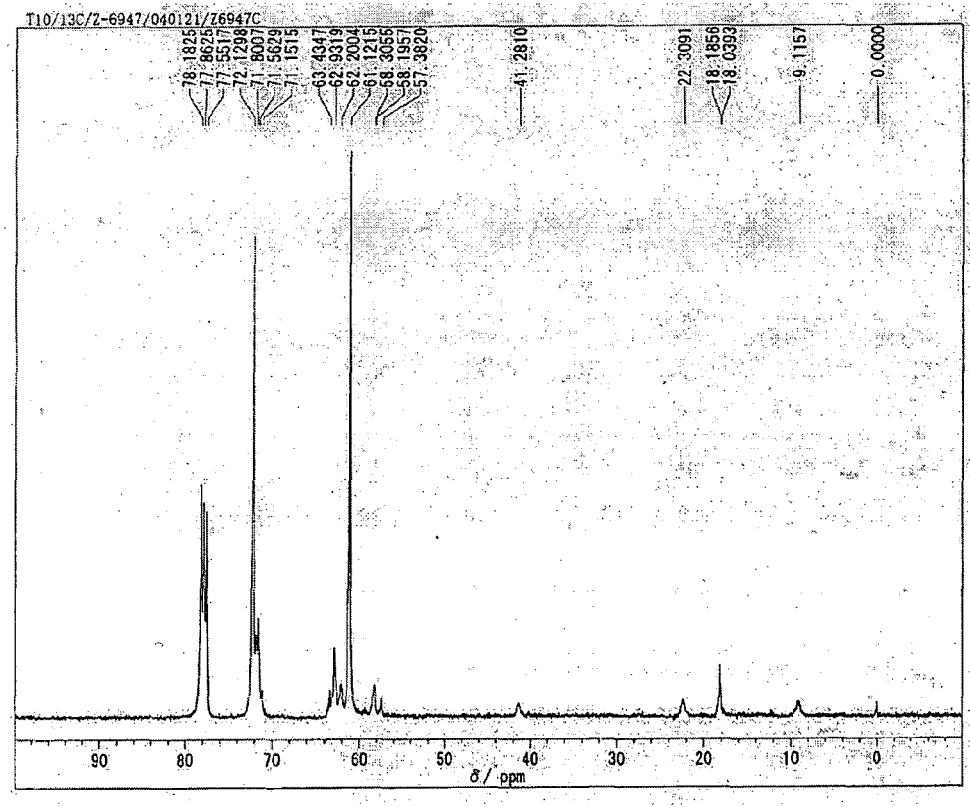
FIG. 4 illustrates a $^{13}$C-NMR chart for the diethyleneglycol solution prepared in EXAMPLE 2.
Figure 5:
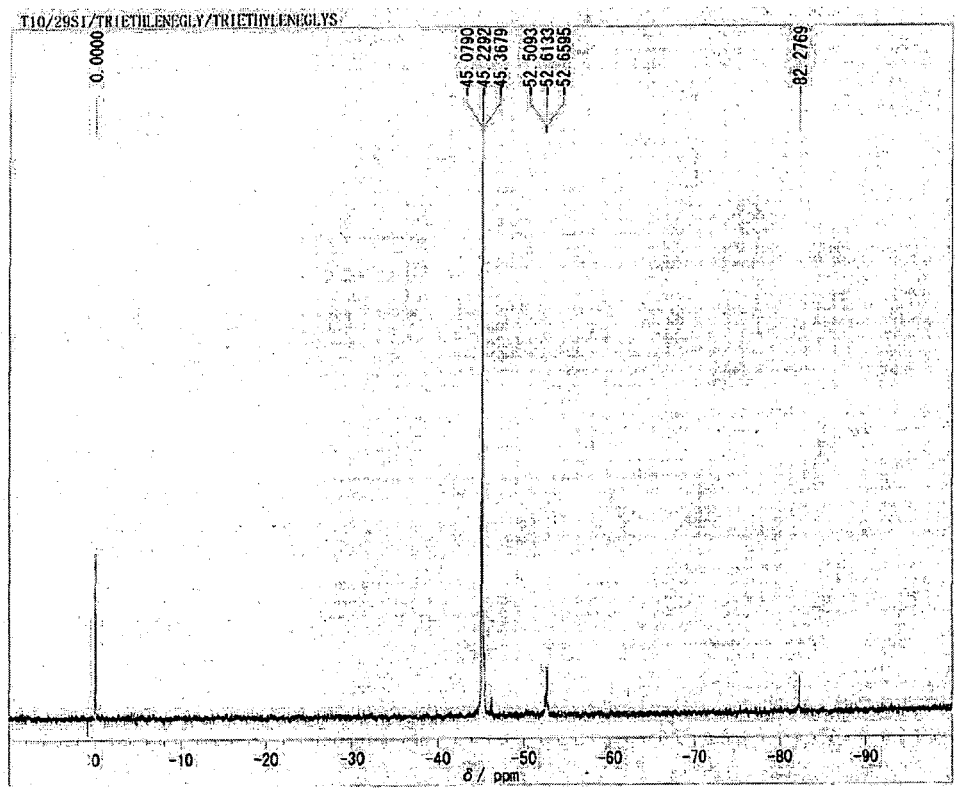
FIG. 5 illustrates a $^{29}$Si-NMR chart for the triethyleneglycol solution prepared in EXAMPLE 3.
Figure 6:
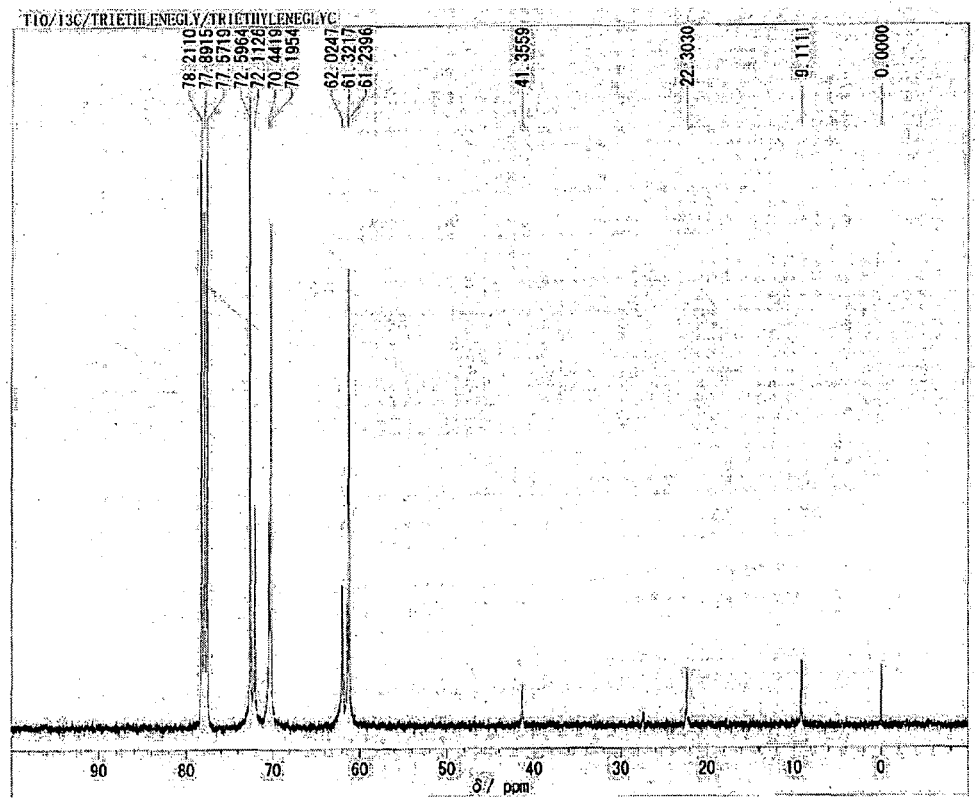
FIG. 6 illustrates a $^{13}$C-NMR chart for the triethyleneglycol solution prepared in EXAMPLE 3.

The present invention relates to the following:

[1] A bis[tri(hydroxypolyalkyleneoxy)silylalkyl] polysulfide represented by general formula (1):

[H(OR$^1$)$_n$O]$_3$SiRS$_x$RSi[O(R$^1$O)$_n$H]$_3$   (1) or

[HO(R$^1$O)$_n$O]$_3$SiRS$_x$RSi[(OR$^1$)$_n$OH]$_3$   (1-1)

(where R is an alkylene group having 1 to 6 carbon atoms; R$^1$ is an alkylene group having 2 to 4 carbon atoms; "n" is 2 or 3; and "x" is an integer from 2 to 8).

[2] A method of manufacturing a bis[tri(hydroxypolyalkyleneoxy)silylalkyl] polysulfide represented by general formula (1):

[H(OR$^1$)$_n$O]$_3$SiRS$_x$RSi[O(R$^1$O)$_n$H]$_3$   (1)

(where R is an alkylene group having 1 to 6 carbon atoms; R$^1$ is an alkylene group having 2 to 4 carbon atoms; "n" is 2 or 3; and "x" is an integer from 2 to 8) by heating a bis[trialkoxysilylalkyl] polysulfide of general formula (2):

(R$^2$O)$_3$SiRS$_x$RSi(OR$^2$)$_3$   (2)

(where R$^2$ is an alkyl group having 1 to 6 carbon atoms, and R and "x" are the same as defined above) together with a polyalkyleneglycol of general formula (3)

H(OR$^1$)$_n$OH   (3)

(where R$^1$ and "n" are the same as defined above) in the presence of an alkali metal alcoholate, thus substituting alkoxy groups represented by formula (4): —OR$^2$ in the alkoxysilyl-containing polysulfide of formula (2) with hydroxypolyalkyleneoxy groups represented by general formula (5):

—O(R$^1$O)$_n$H (where R$^2$, R$^1$, and "n" are the same as defined above).

The present invention also relates to the following:
[3] The method of manufacturing a mixture of a bis[tri(hydroxypolyalkyleneoxy)silylalkyl] polysulfide represented by general formula (1) and a polyalkyleneglycol of general formula (3) by heating a bis[trialkoxysilylalkyl] polysulfide of general formula (2):

(R$^2$O)$_3$SiRS$_x$RSi(OR$^2$)$_3$   (2)

(where R$^2$ is an alkyl group having 1 to 6 carbon atoms, and R and "x" are the same as defined above) together with a polyalkyleneglycol of general formula (3)

H(OR$^1$)$_n$OH   (3)

(where R$^1$ and "n" are the same as defined above) in the presence of an alkali metal alcoholate, thus substituting alkoxy groups represented by formula (4): —OR$^2$ in the alkoxysilyl-containing polysulfide of formula (2) with hydroxypolyalkyleneoxy groups represented by general formula (5):

—O(R$^1$O)$_n$H (where R$^2$, R$^1$, and "n" are the same as defined above), the method being characterized by the fact that the mole number of the polyalkyleneglycol of general formula (3) exceeds the total mole number of alkoxy groups of the bis[trialkoxysilylalkyl] polysulfide of general formula (2).

[4] A tire rubber additive comprising a bis[tri(hydroxypolyalkyleneoxy)silylalkyl] polysulfide represented by general formula (1)

[H(OR$^1$)$_n$O]$_3$SiRS$_x$RSi[O(R$^1$O)$_n$H]$_3$   (1)

(where R is an alkylene having 1 to 6 carbon atoms; R$^1$ is an alkylene group having 2 to 4 carbon atoms; "n" is 2 or 3; and "x" is an integer from 2 to 8) alone or a mixture of the bis[tri(hydroxypolyalkyleneoxy)silylalkyl] polysulfide and a polyalkyleneglycol of general formula (3)

H(OR$^1$)$_n$OH   (3)

(where R$^1$ is an alkylene group having 2 to 4 carbon atoms, and "n" is 2 or 3).

[5] A tire rubber additive obtained by heating a bis[trialkoxysilylalkyl] polysulfide of general formula (2):

(R$^2$O)$_3$SiRS$_x$RSi(OR$^2$)$_3$   (2)

(where R is an alkylene group having 1 to 6 carbon atoms; R$^2$ is an alkyl group having 1 to 6 carbon atoms; and "x" is an integer from 2 to 8) together with a polyalkyleneglycol of general formula (3)

H(OR$^1$)$_n$OH   (3)

(where R$^1$ is an alkylene group having 2 to 4 carbon atoms, and "n" is 2 or 3 and where the mole number of the polyalkyleneglycol of general formula (3) exceeds the total mole number of alkoxy groups of the bis[trialkoxysilylalkyl] polysulfide of general formula (2)), thus substituting alkoxy groups represented by formula (4): —OR$^2$ in the alkoxysilyl-containing polysulfide of formula (2) with hydroxypolyalkyleneoxy groups represented by general formula (5):

—O(R$^1$O)$_n$H (where R$^2$, R$^1$, and "n" are the same as defined above).

The present invention also relates to the following:
[6] A tire rubber composition comprising:
100 parts by weight of an uncured organic rubber (A);
5.0 to 150 parts by weight of a silica filler (B); and
a tire rubber additive (C) as claimed in Item [4] or Item [5] used in an amount of 0.1 to 50 wt. % of the weight of component (B).
[7] A tire rubber composition comprising:
100 parts by weight of an uncured organic rubber (A);
5.0 to 150 parts by weight of silica filler (B);

0.1 to 80 parts by weight of carbon black (D); and
a tire rubber additive (C) as claimed in Item [4] or Item [5] used in an amount of 0.1 to 50 wt. % of the total weight of components (B) and (D).

[8] The tire rubber composition of Item [6] or Item [7], wherein the uncured organic rubber is a uncured diene-type rubber, and the silica filler is a silica filler with reinforcing properties.

[9] The tire rubber composition of Item [8], wherein the uncured diene-type rubber is one selected from the group consisting of an uncured diene/butadiene copolymer rubber, an uncured polybutadiene rubber, an uncured styrene/isoprene copolymer rubber, an uncured styrene/isoprene/butadiene copolymer rubber, uncured acrylonitrile/butadiene copolymer rubber, uncured isoprene rubber, a uncured natural rubber, or a mixture of two or more of the above, and wherein the silica filler with reinforcing properties is a dry-process silica or a wet-process silica.

The bis[tri(hydroxypolyalkyleneoxy)silylalkyl] polysulfide of the present invention is a new silyl-containing polysulfide where hydroxypolyalkyleneoxy groups are used instead of alkoxy groups in a bis(trialkoxysilylalkyl) polysulfide or cyclic alkoxysilyl groups in a bis(cyclic alkoxysilylalkyl) polysulfide. In this case, no environmental problem is caused due to the hydrolysis of the alkoxysilyl groups or cyclic alkoxysilyl groups which is accompanied by generation of low-boiling-point alcohols or alkanediols during mixing with an uncured organic rubber, a silica filler, and other components.

The aforementioned new silyl-containing polysulfide where hydroxypolyalkyleneoxy groups are used instead of alkoxy groups in the bis(trialkoxysilylalkyl) polysulfide or cyclic alkoxysilyl groups in the bis(cyclic alkoxysilylalkyl) polysulfide can be simply and efficiently produced by the method of the present invention.

The tire rubber additive of the present invention makes it possible to solve the environmental problems associated with hydrolysis of alkoxysilyl groups or cyclic alkoxysilyl groups which is accompanied by generation of low-boiling-point alcohols or alkanediols during mixing of an uncured organic rubber, a silica filler, a bis(trialkoxysilylalkyl) polysulfide or bis(cyclic alkoxysilylalkyl) etc. The tire rubber additive of the present invention provides that when the composition is vulcanized, it ensures an increased value of tan δ at 0° C. and a reduced value of tan δ at 60° C. The aforementioned additive also provides excellent balance between wet-skid resistance and low fuel consumption properties and also imparts high wear-resistant properties to the tire.

The rubber composition for tires of the present invention makes it possible to solve the environmental problems associated with hydrolysis of alkoxysilyl groups or cyclic alkoxysilyl groups which is accompanied by generation of low-boiling-point alcohols or alkanediols during mixing of an uncured organic rubber, a silica filler, a bis(trialkoxysilylalkyl) polysulfide or bis(cyclic alkoxysilylalkyl) polysulfide, and other components. Furthermore, the composition when vulcanized provides an increased value of tan δ at 0° C. and a reduced value of tan δ at 60° C., and also provides excellent balance between wet-skid resistance and low fuel consumption properties and also imparts high wear-resistant properties to the tire.

BEST MODE FOR CARRYING OUT THE INVENTION

The bis[tri(hydroxypolyalkyleneoxy)silylalkyl] polysulfide is represented by general formula (1):

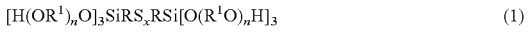

(where R is an alkylene group having 1 to 6 carbon atoms; $R^1$ is an alkylene group having 2 to 4 carbon atoms; "n" is 2 or 3; and "x" is an integer from 2 to 8).

The bis[tri(hydroxypolyalkyleneoxy)silylalkyl] polysulfide can be also represented by general formula (1-1):

(where R is an alkylene group having 1 to 6 carbon atoms; $R^1$ is an alkylene group having 2 to 4 carbon atoms; "n" is 2 or 3; and "x" is an integer from 2 to 8).

Alkylene groups having 1 to 6 carbon atoms are bonded to sulfur atoms on both terminals of the polysulfide having 2 to 8 sulfur atoms, and tri(hydroxypolyalkyleneoxy)silyl groups are bonded to the carbon atoms on the terminals of the aforementioned alkylene groups. Alkylene groups having 1 to 6 carbon atoms are bonded to sulfur atoms on the both terminal of a polysulfide having 2 to 8 sulfur atoms, and tri(hydroxypolyalkyleneoxy)silylalkyl groups are bonded to the carbon atoms on the terminals of the aforementioned alkylene groups.

In the above formula, R designates an alkylene group having 1 to 6 carbon atoms. Such an alkylene group is represented by ethylene, propylene, butylene, pentylene, and hexylene groups. Normally, the propylene, butylene, pentylene, and hexylene groups have a linear molecular structure, but, if necessary, they may have a branched or cyclic molecular structure. From the viewpoint of ease of production, propylene and butylene groups are preferable.

$R^1$ designates an alkylene group having 2 to 4 carbon atoms. Such an alkylene group is represented by ethylene, propylene, and butylene. Normally, this group has a linear molecular structure, but the propylene and butylene groups may have a branched structure as well.

$S_x$ represents a residual polysulfide radical having 2 to 8 sulfur atoms, and alkylene groups having 1 to 6 carbon atoms are bonded to the sulfur atoms on both terminals of the residual polysulfide.

The following are specific examples of tri(hydroxypolyalkyleneoxy)silylalkyl groups in bis[tri(hydroxypolyalkyleneoxy)silylalkyl] polysulfide: tri(hydroxydiethyleneoxy)silylethyl group, tri(hydroxydiethyleneoxy)silylpropyl group, tri(hydroxydipropylenenoxy)silylpropyl group, tri(hydroxydibutylenoxy)silylpropyl group, tri(hydroxydiethyleneoxy)silylbutyl group, and tri(hydroxydipropyleneoxy)silylhexyl group.

The bis[tri(hydroxypolyalkyleneoxy)silylalkyl] polysulfide of the present invention represented by general formula (1):

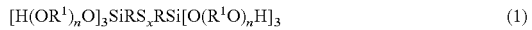

(where R is an alkylene group having 1 to 6 carbon atoms; $R^1$ is an alkylene group having 2 to 4 carbon atoms; "n" is 2 or 3; and "x" is an integer from 2 to 8) is produced by heating the bis[trialkoxysilylalkyl] polysulfide of general formula (2):

(where $R^2$ is an alkyl group having 1 to 6 carbon atoms, and R and "x" are the same as defined above) together with a polyalkyleneglycol of general formula (3):

(where $R^1$ and "n" are the same as defined above) in the presence of an alkali metal alcoholate, thus substituting alkoxy groups represented by formula (4): —$OR^2$ in the bis [trialkoxysilylalkyl] polysulfide of formula (2) with hydroxypolyalkyleneoxy groups represented by general formula (5):

(where $R^2$, $R^1$, and "n" are the same as defined above).

Starting materials for the aforementioned reaction are bis[trialkoxysilylalkyl] polysulfide of general formula (2) and polyalkyleneglycol of general formula (3). The bis[trialkoxysilylalkyl] polysulfide of general formula 2 is exemplified by the following compounds: bis(trimethoxysilylpropyl) disulfide, bis(triethoxysilylpropyl) disulfide, bis(tripropoxysilylpropyl) disulfide, bis(tributoxysilylpropyl) disulfide, bis(trimethoxysilylpropyl) tetrasulfide, bis(triethoxysilylpropyl) tetrasulfide, bis(tripropoxysilylpropyl) tetrasulfide, bis(tributoxysilylpropyl) tetrasulfide, bis(trimethoxysilylbutyl) disulfide, bis(triethoxysilylbutyl) disulfide, bis(tripropoxysilylpropyl) disulfide, bis(tributoxysilylpropyl) disulfide, bis(trimethoxysilylbutyl) tetrasulfide, bis(triethoxysilylbutyl) tetrasulfide, bis(tripropoxysilylbutyl) tetrasulfide, and bis(tributoxysilylbutyl) tetrasulfide.

The polyalkyleneglycol of general formula (3) is the one that has a number of repetitions equal to 2 or 3.

The aforementioned polyalkyleneglycol is exemplified by diethyleneglycol, dipropyleneglycol, dibutyleneglycol, triethyleneglycol, tripropyleneglycol, and tributyleneglycol.

The alkali-metal alcoholate is a catalyst for the reaction of substitution of the silicon-bonded alkoxy groups. Examples of this compound are sodium methoxide, sodium ethoxide, potassium methoxide, potassium ethoxide, and lithium ethoxide.

The mole ratio of the bis[trialkoxysilylalkyl] polysulfide of general formula (2) to the polyalkyleneglycol of general formula (3) is selected so that the mole number of the polyalkyleneglycol of general formula (3) is greater than the total mole number of alkoxy groups contained in the bis[trialkoxysilylalkyl] polysulfide of general formula (2). If the mole number of the polyalkyleneglycol of general formula (3) is either the same as the total mole number of the alkoxy groups contained in the bis[trialkoxysilylalkyl] polysulfide of general formula (2) or is slightly smaller than the aforementioned total number, then the hydroxyl groups of both polyalkyleneglycols will exchange with alkoxy groups of formula (4): —$OR^2$, and a block polymer will be formed due to dealcoholation and condensation of the bis[trialkoxysilylalkyl] polysulfide of general formula (2) and the polyalkyleneglycol of general formula (3). In other words, a solid polymer having a three-dimensional structure is formed, and this creates difficulties for dispersing the additive in the uncured organic rubber and the silica filler.

From this point of view, it is recommended that the mole number of the polyalkyleneglycol of general formula (3) be 1.2 times, preferably 1.5 to 3 times the total mole number of alkoxy groups contained in the bis[trialkoxysilylalkyl] polysulfide of general formula (2). When the mole ratio is maintained in the above range, it becomes possible to effectively mix the bis[tri(hydroxypolyalkyleneoxy)silylalkyl] polysulfide represented by general formula (1) with the polyalkyleneglycol of general formula (3), and, at the same time, to improve conditions for dispersing the above components in the material of the uncured organic rubber. There are no special restrictions in this regard when it is necessary to obtain a solid bis[tri(hydroxypolyalkyleneoxy)silylalkyl] polysulfide.

When a reaction between the bis[trialkoxysilylalkyl] polysulfide of general formula (2) and the polyalkyleneglycol of general formula (3) is conducted under reduced pressure and in the temperature range of 120 to 180° C., it may take from 4 hours to 30 minutes for distilling the alcohol of formula (6): $HOR^2$ that is formed in the process. The alkali-metal alcoholate, which is used as a catalyst for the alkoxy group exchange reaction, should be used in a so-called catalytic amount, and concretely speaking, in an amount of 0.01 to 10 mole %, preferably 0.1 to 2 mole % of the total weight of the bis[trialkoxysilylalkyl] polysulfide of general formula (2). It is recommended to load the alkali-metal alcoholate which is dissolved in a lower alcohol into the bis[trialkoxysilylalkyl] polysulfide of general formula (2) and the polyalkyleneglycol of general formula (3).

The product of the aforementioned reaction comprises bis[tri(hydroxypolyalkyleneoxy)-silylalkyl] polysulfide represented by the general formula (1):

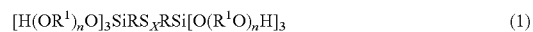  (1)

(where R is an alkylene group having 1 to 6 carbon atoms; $R^1$ is an alkylene group having 2 to 4 carbon atoms; "n" is 2 or 3; and "x" is an integer from 2 to 8).

However, since the mole number of polyalkyleneglycol shown in general formula (3) is greater than the total mole number of alkoxy groups of the bis[trialkoxysilylalkyl] polysulfide of general formula (2), the bis[tri(hydroxypolyalkyleneoxy)silylalkyl] polysulfide of the general formula (1): $[H(OR^1)_nO]_3 SiRS_xRSi[O(R^1O)_nH]_3$ will be obtained in a mixture with the polyalkyleneglycol of general formula (3): $H(OR^1)_nOH$. This reaction product can be used as a tire rubber additive without further treatment.

The tire rubber additive of the present invention comprises a bis[tri(hydroxypolyalkyleneoxy)silylalkyl] polysulfide represented by general formula (1):

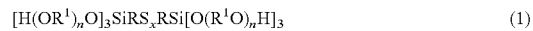  (1)

(where R is an alkylene having 1 to 6 carbon atoms; $R^1$ is an alkylene having 2 to 4 carbon atoms; "n" is 2 or 3; and "x" is an integer from 2 to 8) alone or a mixture of the bis[tri(hydroxypolyalkyleneoxy)silylalkyl] polysulfide and polyalkyleneglycol of general formula (3)

  (3)

(where $R^1$ is an alkylene group having 2 to 4 carbon atoms, and "n" is 2 or 3).

The bis[tri(hydroxypolyalkyleneoxy)silylalkyl] polysulfide that is represented by general formula (1) and that constitutes a tire rubber additive, as well as the method of manufacturing thereof, are described above. The polyalkyleneglycol of general formula (3) and the bis[tri(hydroxypolyalkyleneoxy)silylalkyl] polysulfide represented by general formula (1) contained in the mixture of these components are also described above.

When a reaction occurs between the bis[trialkoxysilylalkyl] polysulfide of general formula (2) and the polyalkyleneglycol of general formula (3) and the mole number of the polyalkyleneglycol of general formula (3) exceeds the total mole number of alkoxy groups contained in the bis[trialkoxysilylalkyl] polysulfide of general formula (2), the mixture of bis[tri(hydroxypolyalkyleneoxy)silylalkyl] polysulfide that is represented by general formula (1) and the polyalkyleneglycol of general formula (3) can be easily formed.

In the mixture of the bis[tri(hydroxypolyalkyleneoxy)silylalkyl] polysulfide represented by general formula (1) and the polyalkyleneglycol of general formula (3), the mole ratio of the aforementioned compounds such that the mixture becomes liquid at room temperature is preferable, for example, the range of (100:1.2) to (100:12) is preferable.

Since the tire rubber additive of the present invention comprises the bis[tri(hydroxypolyalkyleneoxy)silylalkyl] polysulfide that is represented by general formula (1) and since the hydroxypolyalkyleneoxy groups bonded to silicon atoms are used instead of alkoxy groups bonded to silicon atoms, the above additive does not generate highly volatile organic compounds such as lower primary alcohols and alkanediols while being mixed with an uncured organic rubber, silica filler etc. This, in turn, creates improved environmental conditions during preparation of the rubber composition.

The uncured organic rubber (A) which constitutes the main component of the rubber composition for tires of the present invention is usually referred to as "rubber" and is an organic polymer compound that can become an elastic body by vulcanization. There are no special restrictions with regard to this material, provided that it is suitable for manufacturing tires and especially tire treads. The appropriate uncured organic rubber comprises a highly unsaturated organic polymer compound, in particular, a diene-type polymer compound with an iodine number in the range of 20 to 450.

The uncured organic rubber can be exemplified by an uncured styrene/butadiene copolymer rubber, uncured polybutadiene rubber, uncured isoprene/butadiene copolymer rubber, uncured styrene/isoprene copolymer rubber, uncured styrene/isoprene/butadiene copolymer rubber, uncured acrylonitrile/butadiene copolymer rubber, uncured polyisoprene rubber, uncured natural rubber, or a similar uncured conjugated diene-type rubber, uncured chloroprene rubber, and uncured partially-hydrogenated diene-type rubber, and a mixture of such uncured rubbers.

In the rubber composition of the present invention, silica filler (B) and carbon black (D) are fillers that are used for reinforcing the rubber obtained after vulcanization. The silica filler preferably comprises reinforcing silica filler such as fumed silica (dry-process silica) or precipitated silica (wet-process silica). These fillers may be hydrophobized by treating their surfaces with an organic silicon compound such as hexamethyldisilazane, dimethyldichlorosilane, trimethylchlorosilane, or octamethyltetracyclosiloxane. Carbon black may comprise the one normally used for rubber reinforcement and may be represented, e.g., by furnace black, channel black, lamp black, thermal black, or acetylene black. Carbon black can be used in a pellet-type form or in the form of non-pelletized aggregated lumps.

Component (B) is used in an amount of 5 to 150 parts by weight, preferably 10 to 100 parts by weight, and most preferably, 30 to 90 parts by weight per 100 parts by weight of component (A). When carbon black (D) is used, it should be added in an amount of 0.1 to 80 parts by weight and, preferably, 5 to 50 parts by weight per 100 parts by weight of component (A). However, the total weight of components (B) and (D) should not exceed 120 parts by weight per 100 weight of component (A). If the aforementioned filler is added in amounts less than the recommended lower limit, the obtained rubber will not be sufficiently strong. If, on the other hand, the added amount exceeds the recommended range, this will create difficulties for mixing and kneading the fillers with component (A).

Component (C) is added in an amount of 0.1 to 50 wt. %, preferably, 0.1 to 30 wt %, and more preferably 5.0 to 30 wt % per weight of component (B), or in an amount of 0.1 to 50 wt. %, preferably, 0.1 to 30 wt. %, and more preferably 5.0 to 30 wt % per total weight of components (B) and (D).

It is recommended that component (C) which is dissolved in the polyalkyleneglycol of general formula (3) is mixed with components (A) and (B). This improves dispersibility in components (A) and (B). Concentration of component (C) in the solution is preferably in the range of 30 to 95 wt. %.

Various methods can be used for adding component (C). For example, component (C) can be pre-mixed with component (B) and then the mixture is added and mixed with component (A). Alternatively, component (C) can be added to a mixture of components (A) and (B).

The following are examples of the most preferable (C) bis[tri(hydroxypolyalkyleneoxy)silylalkyl] polysulfide used in the rubber composition of the present invention.

[I] Bis[tri(hydroxydiethyleneoxy)silylpropyl] disulfide

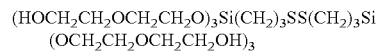

(HOCH$_2$CH$_2$OCH$_2$CH$_2$O)$_3$Si(CH$_2$)$_3$SS(CH$_2$)$_3$Si(OCH$_2$CH$_2$OCH$_2$CH$_2$OH)$_3$   Formula 1

[II] Bis[tri(hydroxydiethyleneoxy)silylpropyl] tetrasulfide

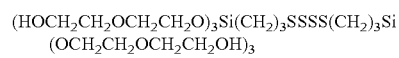

(HOCH$_2$CH$_2$OCH$_2$CH$_2$O)$_3$Si(CH$_2$)$_3$SSSS(CH$_2$)$_3$Si(OCH$_2$CH$_2$OCH$_2$CH$_2$OH)$_3$   Formula 2

[III] Bis[tri(hydroxytriethyleneoxy)silylpropyl] disulfide

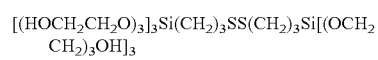

[(HOCH$_2$CH$_2$O)$_3$]$_3$Si(CH$_2$)$_3$SS(CH$_2$)$_3$Si[(OCH$_2$CH$_2$)$_3$OH]$_3$   Formula 3

If necessary, the rubber composition for tires of the present invention may be combined with other conventional additives such as weight-increasing fillers, organic fibers, naphthene-type process oil or similar softeners, pigments, foaming agents, ultraviolet-ray absorbers, aging inhibitors, antioxidants, scorch inhibitors, waxes, etc. There are no special restrictions with regard to the amounts in which these additives can be added to the rubber composition, and optional amounts can be appropriately selected, provided that the additives in the selected amounts do not adversely affect tire performance.

The rubber composition for tires of the present invention can be produced by methods known in the art. The components of the composition can be uniformly mixed and kneaded in a Banbury mixer, two-axis roller, kneader-mixer, two-axis extruder, etc. During mixing, the rubber composition has preferably a temperature in the range of 120 to 180° C.

Vulcanization agents such as sulfur, insoluble sulfur, sulfur compound, etc., are added to the composition in a two-roll mill, two-axis extruder, etc., for vulcanizing the composition and forming tires, and especially tire treads. If necessary, vulcanization-assisting agents and vulcanization accelerators can also be added. The vulcanization assistants may comprise zinc oxide, stearic acid, etc. The vulcanization accelerators may comprise mercaptobenzothiazol (MBT), benzothiazyldisulfide (MBTS), N-tert-butyl-2-benzothiazolylsulfenamide (TBBS), N-cyclohexyl-2-benzothiazyl-sulfinamide (CBS), or similar thiazol-type accelerators. Because too much temperature elevation during mixing may cause premature vulcanization, it is recommended to mix with cooling. The rubber composition that contains the vulcanization agent and, if necessary, other additives, is subjected to heat-molding in a mold. If necessary, after primary vulcanization, the vulcanizate is subjected to a secondary vulcanization.

Component (C) consists of a bis[tri(hydroxypolyalkyleneoxy)silylalkyl] polysulfide of general formula (1), and because the silicon-bonded alkoxy groups are replaced with hydroxypolyalkyleneoxy groups, mixing of components (A), (B), and (C) or components (A), (B), (C), and (D) is carried out without the formation of highly volatile organic compounds such as lower primary alcohols and alkanediols. Therefore, the rubber composition for tires of the present invention can be prepared under improved environmental conditions.

Tires produced by vulcanizing the rubber composition of the present invention can be used as automobile tires, aircraft tires, bicycle tires, etc., but the most preferable is passenger-car tires, track tires, race-car tires, and aircraft tires.

EXAMPLES

The present invention is further described with reference to practical examples and comparative examples. In the practical examples, $^{29}$Si-NMR measurements of diethyleneglycol solutions and triethyleneglycol solutions were carried out in deuterium chloroform by using a JEOL JNM-EX400 spectrometer (product of JEOL.CO.JP) and employing tetramethylsilane as an internal reference.

$^{13}$C-NMR measurements of diethyleneglycol solutions and triethyleneglycol solutions formed in the process were also carried out in deuterium chloroform by using the JEOL JNM-EX400 spectrometer and employing tetramethylsilane as an internal reference. The presence of hydroxypolyalkyleneoxysilyl groups in the bis[tri(hydroxypolyalkyleneoxy)silylalkyl] polysulfide was detected in the same manner as above by observing peaks in $^{29}$Si-NMR and $^{13}$C-NMR charts. The amount of the bis[tri(hydroxypolyalkyleneoxy)silylalkyl] polysulfide formed in the solution was calculated through the ratio with the starting material used in the process. Weights are given in terms of wt. %.

Example 1

Preparation of a 72% Diethyleneglycol Solution of Bis[tri(hydroxydiethyleneoxy)silylpropyl] disulfide represented by

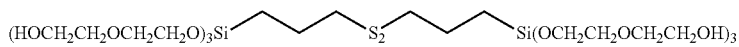
(HOCH$_2$CH$_2$OCH$_2$CH$_2$O)$_3$Si~~~~S$_2$~~~~Si(OCH$_2$CH$_2$OCH$_2$CH$_2$OH)$_3$ A glass flask equipped with a stirrer and thermometer was filled with 332.4 g (0.70 mole) of bis[tri(ethoxy)silylpropyl] disulfide, 668.6 g (6.30 moles) of diethyleneglycol, and 2.38 g (0.0070 mole) of a 20% ethanol solution of sodium ethoxide. While the pressure was gradually reduced to 200 mmHg, the components were stirred for 2 hours at 150° C. After two hours of stirring, the pressure was further reduced, the ethanol formed in the process was removed by means of distillation, and, as a result, 802.7 g of the aforementioned solution were obtained with a yield of 99%.

Example 2

Preparation of a 73% Diethyleneglycol Solution of Bis[tri(hydroxydiethyleneoxy)silylpropyl] tetrasulfide represented by

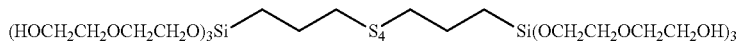
(HOCH$_2$CH$_2$OCH$_2$CH$_2$O)$_3$Si~~~~S$_4$~~~~Si(OCH$_2$CH$_2$OCH$_2$CH$_2$OH)$_3$ A glass flask equipped with a stirrer and thermometer was filled with 377.3 g (0.70 mole) of bis(triethoxysilylpropyl) tetrasulfide, 668.4 g (6.30 moles) of diethyleneglycol, and 2.38 g (0.0070 mole) of a 20% ethanol solution of sodium ethoxide. While the pressure was gradually reduced to 200 mmHg, the components were stirred for 2 hours at 150° C. After two hours of stirring, the pressure was further reduced, the ethanol formed in the process was removed by means of distillation, and, as a result, 852.2 g of the aforementioned solution were obtained with a yield of 99%.

Example 3

Preparation of a 71% Triethyleneglycol Solution of Bis[tri(hydroxytriethyleneoxy)silylpropyl] disulfide represented by

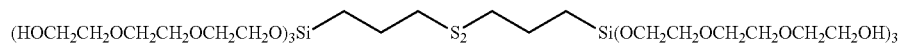
(HOCH$_2$CH$_2$OCH$_2$CH$_2$OCH$_2$CH$_2$O)$_3$Si~~~~S$_2$~~~~Si(OCH$_2$CH$_2$OCH$_2$CH$_2$OCH$_2$CH$_2$OH)$_3$ A glass flask equipped with a stirrer and thermometer was filled with 47.5 g (0.10 mole) of bis(triethoxysilylpropyl) disulfide, 135.2 g (0.90 mole) of triethyleneglycol, and 0.34 g (0.0010 mole) of a 20% ethanol solution of sodium ethoxide. While the pressure was gradually reduced to 200 mmHg, the components were stirred for 2 hours at 150° C. After two hours of stirring, the pressure was further reduced, the ethanol formed in the process was removed by means of distillation, and, as a result, 77.3 g of the aforementioned solution were obtained with a yield of 99%.

Example 4 and Comparative Example 1

The rubber composition for Test Piece A and a rubber composition for Test Piece C were prepared from components shown in Table 1.

TABLE 1

| Components | EXAMPLE 4 Composition for Test Piece A | COMPARATIVE EXAMPLE 1 Composition for Test Piece C |
|---|---|---|
| SBR (JSR1500) | 100 | 100 |
| HAF Carbon (Asahi # 70) | 5 | 5 |
| Nipsil AQ | 40 | 40 |
| Zinc Oxide, Type 2 | 3 | 3 |
| Diethyleneglycol Solution of EXAMPLE 2 | 9 | — |
| Diethyleneglycol | — | 2.5 |
| Stearic Acid | 2 | 2 |
| NOCRAC 810-NA | 1 | 1 |
| NOCCELER-CZ | 1.2 | 1.2 |
| NOCCELER-D | 1.5 | 1.5 |
| Sulfur Powder | 1.5 | 1.5 |

A more detailed description of the aforementioned components is given below in Table 2.

TABLE 2

| | |
|---|---|
| SBR (JSR1500) | Emulsion-polymerized styrene butadiene rubber, product of JSR Co. Stabilizer: ST; Bonded Styrene: 23.5%; Mooney viscosity ML1 + 4 (100° C.): 52; Emulsifier: RA; Coagulant: salt-acid, Specific Gravity: 0.94 |
| HAF Carbon (Asahi # 70) | product of Asahi Carbon Co, Ltd. average particle size: 28 nm, specific surface area: 77 m$^2$/g, iodine adsorption: 80 mg/g, DBP adsorption(A method): 101 ml/100 g, heating loss: 0.3%, volatile content: 1.3% |
| Nipsil AQ | Nipsil is a registered trademark of TOSOH SILICA CORPORATION, Precipitated silica (microgranule-type highly active product), product of TOSOH SILICA CORPORATION |
| Zinc Oxide, Type 2 | Grain size: 0.2 to 0.6 μm; product of MISTUI MINING & SMELTING CO., LTD. |
| Stearic Acid | Product of NOF CORPORATION |
| NOCRAC 810-NA | NOCRAC is a registered trademark of Ouchi Saimo Trading Co., N-phenyl-N-isopropyl-p-phenylenediamine, Phenylisopropyl-p-phenylenediamine, 1-phenylamino-4-isopropylaminobenzene, product of OUCHI SHINKO CHEMICAL INDUSTRIAL, Aromatic secondary amine-type antiaging agent and crack-preventing agent for NR, IR, BR, SBR, NBR, CR |
| NOCCELER-CZ | NOCCELER-CZ-G, NOCCELER is a registered trademark of Ouchi Saimo Trading Co., N-cyclohexyl-2-benzothiazolyl-sulfenamide, JIS K 6202, product of OUCHI SHINKO CHEMICAL INDUSTRIAL, sulfenamide-type delayed effective vulcanization accelerator for NR, IR, BR, SBR, NBR, CR |
| NOCCELER-D | NOCCELER-D-P, 1,3-diphenylguanidine, N,N'diphenylguanidine, product of OUCHI SHINKO CHEMICAL INDUSTRIAL, guanidine-type vulcanization accelerator for NR, IR, BR, SBR, NBR, CR |
| Sulfur Powder | Product of Kawagoe Chemical Co. |

In the preparation of the rubber composition, mixing and kneading of the components were carried out in accordance with JIS K6299 "Preparation of Test Pieces for Testing Rubber"

Mixing and Kneading Conditions (One-step kneading in a tightly sealed kneader)
   Test machine—Laboplast Mill—100C 100 type
   Rotor: B600 (Banbury type, 600 cm$^3$)
   Rotor speed: 50 rpm
   Filling rate: 70%
   Set temperature: 120° C.
   Maximal temperature at the exit: 150° C.
   Duration of kneading: 4 min.
     (Two-stage kneading: roller-type kneading machine)
   Roller dimensions: diameter. 8"×18"
   Front roller speed: 20 rpm
   Front/rear roller speed ratio: 1:1.5

Each aforementioned composition was vulcanized under the following condition.
   Sheet
   Test Piece A: 160° C.×11 min.
   Test Piece C: 160° C.×18 min.
   Block
   Test Piece A: 160° C.×16 min.
   Test Piece C: 160° C.×23 min.

Characteristics of the rubber compositions for aforementioned test pieces and characteristics of the rubbers obtained by vulcanizing the rubber compositions were measured under conditions given below. The results of measurements are shown in Table 3.

<Methods of Measuring Characteristics of Rubber Compositions and Rubbers>

1. Mooney Viscosity

This characteristic was measured in accordance with the provisions of JIS K6300 "Physical testing methods for unvulcanized rubber"
   Measurement temperature: 100° C.
   Die vulcanization test-A method
   Oscillation amplitude: ±1°, oscillation frequency: 1.67 Hz 2. Elongation (%)

This characteristic was measured in according with the provisions of JIS K6251 "Method of testing tensile strength of vulcanized rubber".
   Specimen: JIS No. 3 for tensile test 3. Tear Strength (N/mm)

This characteristic was measured in according with the provisions of JIS K6252 "Method of testing tear strength of vulcanized rubber".
   Specimen: angle-shaped without slitting (perpendicular to grain direction).

4. Hardness (Durometer Hardness)

This characteristic was measured in according with the provisions of JIS K6253 "Method of testing hardness of vulcanized rubber and thermoplastic rubber".

5. Worn Volume (cm$^3$)

This characteristic was measured by the Acron wear method test (A-2) in according with the provisions of JIS K6264 "Method of testing wear of vulcanized resin".
   Load: 44.1N (4.50 kgf)
   Angle: 10°
   Preliminary test: 500 revolutions
   Basic test: 1000 revolutions 6. Tan δ

This characteristic was measured in according with the provisions of JIS K7244-4 "Method of testing dynamic characteristics of plastics—Part 4: Tensile vibrations—Non-resonant vibration method".
   Measured items: dynamic storage modulus of elasticity E'
     dynamic loss modulus of elasticity E"
     tangent of loss tan δ

Sample dimensions: 1 mm×5 mm×30 mm
Measurement mode: tensile mode
Measurement frequency: 10 Hz
Heating rate: 2° C./min
Measurement temperature: 0° C., 60° C.
Dynamic strain: 0.1%
Tester: Viscosity measuring instrument RSA-II, the product of Rheometrics Co.

7. Characteristic Balance

The ratio of aforementioned tan δ (0° C.) to tan δ (60° C.) is indicated as (0° C./60° C.). The greater is the ratio, the better is the tire balance (wet skidding and low fuel consumption properties).

Results of the test of specimens "A" and "C" are shown in Table 3.

TABLE 3

| Type of test | Test conditions | EXAMPLE 4 Test Piece A | COMPARATIVE EXAMPLE 1 Test Piece C |
|---|---|---|---|
| Mooney Viscosity Test | ML1 + 4 (100° C.) | 76 | 70 |
| Vulcanization test with the use of vibration-type vulcanization tester (curastometer, type III, 160° C.) | Minimal value (N · m) | 0.27 | 0.19 |
| | Maximal value (N · m) | 1.62 | 1.73 |
| | $T_{10}$ (min.) | 1.3 | 5.3 |
| | $T_{50}$ (min.) | 1.9 | 7.9 |
| | $T_{90}$ (min.) | 6.3 | 13.0 |
| Hardness test | Durometer hardness | A68 | A70 |
| Tensile test | Tensile strength (MPa) | 32.0 | 26.4 |
| | Elongation (%) | 640 | 500 |
| | 100% tensile stress (MPa) | 2.18 | 2.34 |
| | 200% tensile stress (MPa) | 4.91 | 5.68 |
| | 300% tensile stress (MPa) | 9.14 | 11.4 |
| | 400% tensile stress (MPa) | 14.6 | 18.4 |
| | 500% tensile stress (MPa) | 20.6 | 26.4 |
| Tear test | Tear strength (N/mm) | 58.4 | 59.4 |
| Wearability test (Acron system) | Worn volume (cm³) | 0.016 | 0.021 |
| Viscoelasticity test | tan δ at 0° C. | 0.211 | 0.132 |
| | tan δ at 60° C. | 0.103 | 0.086 |
| | Ratio of tan δ (0° C.) to tanδ (60° C.) | 2.05 | 1.53 |

INDUSTRIAL APPLICABILITY

The bis[tri(hydroxypolyalkyleneoxy)silylalkyl] polysulfide of the present invention is suitable for use as an additive to rubber compositions and, especially, to tire rubber compositions.

The manufacturing method of the present invention is suitable for simple and efficient manufacture of a new silyl-containing polysulfide that contains silicon-bonded hydroxypolyalkyleneoxy groups instead of alkoxy groups in the bis(trialkoxysilylalkyl) polysulfide or cyclic alkoxysilyl groups in the bis(cyclic alkoxysilylalkyl) polysulfide. The tire rubber additive of the present invention improves properties of the tire rubber. The tire rubber composition of the present invention can be used for manufacturing tires such as automobile tires and aircraft tires.

The invention claimed is:

1. A method of manufacturing a bis[tri(hydroxypolyalkyleneoxy)silylalkyl] polysulfide represented by general formula (1):

$$[H(OR^1)_nO]_3 SiRS_xRSi[O(R^1O)_nH]_3 \quad (1)$$

where R is an alkylene group having 1 to 6 carbon atoms; $R^1$ is an alkylene group having 2 to 4 carbon atoms; "n" is 2 or 3; and "x" is an integer from 2 to 8, by heating a bis[trialkoxysilylalkyl] polysulfide of general formula (2):

$$(R^2O)_3SiRS_xRSi(OR^2)_3 \quad (2)$$

where $R^2$ is an alkyl group having 1 to 6 carbon atoms, and R and "x" are the same as defined above, together with a polyalkyleneglycol of general formula (3):

$$H(OR^1)_nOH \quad (3)$$

where $R^1$ and "n" are the same as defined above, in the presence of an alkali metal alcoholate, thus substituting alkoxy groups represented by formula (4): —$OR^2$ in the bis[trialkoxysilylalkyl]polysulfide of formula (2) with hydroxypolyalkyleneoxy groups represented by general formula (5): —$O(R^1O)_nH$
where $R^2$, $R^1$, and "n" are the same as defined above.

2. A method of manufacturing a mixture of a bis[tri(hydroxypolyalkyleneoxy)silylalkyl] polysulfide represented by general formula (1):

$$[H(OR^1)_nO]_3SiRS_xRSi[O(R^1O)_nH]_3 \quad (1)$$

where R is an alkylene group having 1 to 6 carbon atoms; $R^1$ is an alkylene group having 2 to 4 carbon atoms; "n" is 2 or 3; and "x" is an integer from 2 to,
and a polyalkyleneglycol of general formula (3) by heating a bis[trialkoxysilylalkyl] polysulfide of general formula (2):

$$(R^2O)_3SiRS_xRSi(OR^2)_3 \quad (2)$$

where $R^2$ is an alkyl group having 1 to 6 carbon atoms, and R and "x" are the same as defined above, together with a polyalkyleneglycol of general formula (3):

$$H(OR^1)_nOH \quad (3)$$

where $R^1$ and "n" are the same as defined above, in the presence of an alkali metal alcoholate, thus substituting alkoxy groups represented by formula (4): —$OR^2$ in the alkoxysilyl-containing polysulfide of formula (2) with hydroxypolyalkyleneoxy groups represented by general formula (5): —$O(R^1O)_nH$
where $R^2$, $R^1$, and "n" are the same as defined above, the method being characterized by the fact that the mole number of the polyalkyleneglycol of general formula (3) exceeds the total mole number of alkoxy groups of the bis [trialkoxysilylalkyl] polysulfide of general formula (2).

3. The method of manufacturing the mixture according to claim 2, wherein the mole number of the polyalkyleneglycol of general formula (3) is at least 1.2 times the total mole number of alkoxy groups of the bis [trialkoxysilylalkyl] polysulfide of general formula (2).

4. The method of manufacturing the mixture according to claim 2, wherein the mole number of the polyalkyleneglycol of general formula (3) is 1.5 to 3 times the total mole number of alkoxy groups of the bis [trialkoxysilylalkyl] polysulfide of general formula (2).

* * * * *